United States Patent
Weise

(10) Patent No.: US 6,444,238 B1
(45) Date of Patent: Sep. 3, 2002

(54) PAIN RELIEF COMPOSITION AND METHOD OF RELIEVING PAIN

(75) Inventor: Richard Weise, Fort Worth, TX (US)

(73) Assignee: General Cosmetics Corporation, New York, NY (US)

(*) Notice: Subject to any disclaimer, the term of this patent is extended or adjusted under 35 U.S.C. 154(b) by 0 days.

(21) Appl. No.: 09/522,581

(22) Filed: Mar. 10, 2000

(51) Int. Cl.⁷ .......................... A01N 65/00; A61K 35/78
(52) U.S. Cl. ....................... 424/736; 424/725; 424/742; 424/744; 424/747
(58) Field of Search ................. 424/725, 736, 424/744, 747, 742

(56) References Cited

U.S. PATENT DOCUMENTS

| | | | |
|---|---|---|---|
| 4,163,049 A | 7/1979 | Aubin | 424/59 |
| 4,671,959 A | 6/1987 | Warren et al. | 424/195.1 |
| 5,223,269 A | 6/1993 | Liepins | 424/600 |
| 5,236,722 A | 8/1993 | Schroeder | 426/67 |
| 5,266,318 A * | 11/1993 | Taylor-McCord | 424/401 |
| 5,294,434 A | 3/1994 | King et al. | 524/58 |
| 5,346,697 A | 9/1994 | Tokuyama et al. | 424/195.1 |
| 5,378,465 A | 1/1995 | Zeines | 424/195.1 |
| 5,401,728 A | 3/1995 | Simon | 514/78 |
| 5,587,191 A | 12/1996 | Donsbach et al. | 426/66 |
| 5,747,079 A | 5/1998 | Hoffman | 426/67 |
| 5,855,921 A | 1/1999 | Somlyai | 424/600 |
| 5,888,984 A | 3/1999 | Brown | 514/54 |
| 5,997,876 A * | 12/1999 | Shikhashvili et al. | 424/443 |

OTHER PUBLICATIONS

Castleman "The Healing Herbs" Aloe pp. 42–44 Rodale Press Emmaus, PA 1991.*

* cited by examiner

Primary Examiner—Herbert J. Lilling
(74) Attorney, Agent, or Firm—Patterson, Thuente, Skaar & Christensen, P.A.

(57) ABSTRACT

A pain relief composition and a method of relieving pain in a human body. The method includes preparing a pain relief composition from a mixture of aloe vera oil, eucalyptus oil, lemon oil, orange oil, peppermint oil, and rosemary oil. The method also includes topically applying the pain relief composition to the human body proximate to where a person is experiencing discomfort.

9 Claims, No Drawings

PAIN RELIEF COMPOSITION AND METHOD OF RELIEVING PAIN

FIELD OF THE INVENTION

The present invention relates generally to a composition for relieving pain and the use of the same for relieving pain. More particularly, the present invention relates to a composition that contains a mixture of essential oils and that is used for treating pain in a human body.

BACKGROUND OF THE INVENTION

As people attempt to accomplish increasingly accomplish more things both professionally and personally in specified periods of time, people get frustrated when physical ailments prevent them from operating near peak efficiencies. For example, many women experience significant amounts of discomfort at selected times during their menstrual cycles. Such conditions are often identified as premenstrual syndrome ("PMS").

Conventional pain relievers such as aspirin and acetaminophen have produced only moderate success in addressing the physical symptoms associated with PMS. There have been numerous attempts at preparing pain relievers that exhibit a greater efficacy in treating PMS. However, these treatments do not produce advantageous results on a significant proportion of the population.

As such, it is frequently necessary for people who suffer from significant PMS discomfort levels to obtain treatment from a physician who often must prescribe stronger medications to reduce the discomfort to an acceptable level. A drawback associated with the use of such stronger medications is that these type of medications often negatively affect the patient's mental and/or physical acuity.

In light of the recurring nature of PMS, ongoing episodes in which a person experiences a significant level of discomfort from PMS can lead to a noticeable decrease in the person's long-term productivity, possibly even threatening the person's ability to remain gainfully employed.

In addition to minimizing the use of medications that negatively affect mental and/or physical acuity, it is also desirable to reduce or eliminate the use of non-natural medications, as such medications are believed to cause other less desirable physical ailments such as cancer.

SUMMARY OF THE INVENTION

The present invention is a method of treating pain in a human body. The method includes preparing a pain relief composition from a mixture of aloe vera oil, eucalyptus oil, lemon oil, orange oil, peppermint oil, and rosemary oil. The method also includes topically applying the pain relief composition to the human body proximate to where a person is experiencing discomfort.

DETAILED DESCRIPTION OF THE INVENTION

While the present invention is susceptible of embodiments in various forms, there is hereinafter be described presently preferred embodiments with the understanding that the present disclosure is to be considered an exemplification of the invention and is not intended to limit the invention to the specific embodiments described.

The present invention is a composition that relieves pain when applied topically to the human body proximate the location of the pain. For example, the pain relief composition of the present invention is particularly suited for relieving pain associated with PMS when the pain relief composition is applied to the person's abdomen.

The pain relief composition of the present invention is also useful in treating other physical ailments, such as muscle strains, muscle sprains, muscle aches, headaches, bruises, arthritis, and joint pain. Additionally, the pain relief composition reduces swelling when applied topically in areas of a body where swelling is found.

The pain relief composition of the present invention is formulated from organically derived essential oils. As such, the pain relief composition provides consumers with a technique to reduce the level of pain while not using artificial, man-made compositions. The organically-derived nature of the composition of the present invention has substantial value to those individuals who desire to reduce pain without using artificial, man-made compositions.

The pain relief composition is substantially a mixture of essential oils. Essential oils used in preparing the pain relief composition of the present invention include aloe vera, peppermint, lemon, orange, and rosemary oils. The concentration of aloe vera oil is between about 10 and 18 percent by weight and preferably between about 13 and 16 percent by weight. The concentration of eucalyptus oil is between about 0.5 and 5 percent by weight and preferably between about 1 and 3 percent by weight. The concentration of lemon oil is between about 0.5 and 5.0 percent by weight and preferably about 1 and 3 percent by weight. The concentration of orange oil is between about 0.5 and 5.0 percent by weight and preferably about 1 and 3 percent by weight. The concentration of peppermint oil is between about 65 and 80 percent by weight and preferably between about 70 and 75 percent by weight. The concentration of rosemary oil is between about 2 and 10 percent by weight and preferably about 4 and 7 percent by weight.

The composition of the present invention also preferably includes calendula oil (Calendula officinalis), which is derived from the marigold plant. The concentration of calendula oil is up to about 25 percent by weight and preferably about 20 percent by weight.

A person of ordinary skill in the art will appreciate that it is possible to utilize additional essential oils in the pain relief composition without departing from the scope of the present invention. One such additional oil is camphor oil, which my be used at a concentration of up to 5 percent by weight. Another suitable essential oil is tagette oil.

Aloe vera oil is obtained from the dried leaves of Aloe barbadensis Miller (Aloe vera Linnè).

Camphor oil contains bicyclo [2.2.1] heptan-2-one, 1,7,7-trimethyl-, 2-Camphanone; 2-Bomanone [76-22-2] $C_{10}H_{16}O$. Camphor oil is preferably obtains by steam distilling chips of the camphor tree and then purifying the material thereby obtained.

Eucalyptus oil contains not less than 70 percent by weight of $C_{10}H_{18}O$ (eucalyptol). Other components typically found in eucalyptus oil include d-a-pinene, globulol, pinocarveol, pinocarvone, and selected aldehydes. Eucalyptus oil has a specific gravity of between about 0.905 and 0.925 at 25° C. Eucalyptus oil is preferably obtained by distilling fresh leaves of Eucalyptus globulus Labillardière or other species of Eucalyptus L' Heritier (Fan Myrtaceae).

Lemon oil typically contains citral, d-limonene, l-α-pinene, β-pinene, camphene, β-phellandrene and γ-terpinene. The total aldehyde content of lemon oil, calculated as citral ($C_{10}H_{16}O$), is between about 2.2 and 5.5 percent. Lemon oil has a specific gravity of between about 0.849 and 0.855 at 25° C. Lemon oil is obtained by expression from the fresh peel of the fruit of Citrus limon (Linnè) Burmann filius (Fam Rutaceae).

Orange oil consists of at least 90 percent by weight d-limonene along with other odorous constituents such as n-decylic aldehyde, citral, d-linalool, n-nonyl alcohol and traces of esters of formic, acetic, caprylic and capric acids. The total aldehyde content, calculated as decanal ($C_{10}H_{20}O$), is between about 1.2 and 2.5 percent. Orange oil has a specific gravity of between about 0.842 and 0.846 at 25° C. Orange oil is prepared by expression from the fresh peel of the ripe fruit of Citrus sinensis (Linnè) Osbeck (Fam Rutaceae).

Peppermint oil contains not less than 5 percent of esters, calculated as menthyl acetate ($C_{12}H_{22}O_2$), and not less than 50 percent of total menthol ($C_{10}H_{20}O$), free and as esters. Other components typically found in peppermint oil include methone, piperitone, α-pinene, 1-limonene, phellandrene, cadinene, menthyl isovalerate isovaleric aldehyde, acetaldehyde, menthofuran, cineol, an unidentified lactone ($C_{10}H_{16}O_2$), and amyl acetate. Peppermint oil is distilled with steam from the fresh overground parts of the flowering plant of Mentha piperia Linnè(Fam Labiatae). Peppermint oil has a specific gravity of between about 0.896 and 0.908 at 25° C.

Rosemary oil contains not less than 1.5 percent of esters calculated as bornyl acetate ($C_{12}H_{20}O_2$), and not less than 8 percent of total borneol ($C_{10}H_{18}O$), free and as esters. Cineol is present at a concentration of between 19 and 25 percent by weight. Terpenes d- and l-α-pinene, dipentene and camphene, and the ketone camphor also occur in rosemary oil. Rosemary oil is distilled with steam from the fresh flowering tops of Rosemarinus officinalis Linnè(Fam Labiatae). Rosemary oil has a specific gravity of between about 0.894 and 0.912 at 25° C.

As a preliminary step in preparing the pain relief composition of the present invention, each of the components is put through a subjective quality control evaluation in which the color, smell and weight are evaluated. These results are then compared with previous samples of the same components to ensure that each of the essential oils of the same quality as the previously used components.

Next, each of the components is separately filtered to remove any particulate matter contained therein. Filtering is preferably accomplished by passing the components through a Grade 2 filter.

The components are then warmed to a temperature of between about 30 and 40° C. and preferably between about 35 and 38° C. so that each of the components is at approximately the same temperature. Providing each of the components at approximately the same temperature when the components are mixed eliminates or significantly reduces undesirable interactions between the components.

The order in which the components are mixed is also believed to play an important role in preparing a stable composition. The components are mixed together based on the hydrophil content. The components with the highest hydrophil content are mixed together first followed by the components with the lower hydrophil content.

The hydrophil content of the essential oils used in producing the pain relief composition tend to vary based upon several factors including the location in which the plant that was used to produce the essential oil was grown. As such, the hydrophil content should be monitored with each group of materials.

The hydrophil content is preferably determined by evaluating each material in a gas chromatograph. Typically, peppermint oil has the highest hydrophil content of about 40–45 percent. The hydrophil content of rosemary oil is typically about 18. The hydrophil content of eucalyptus oil is typically about 11 percent.

After the addition of each component, the mixture is sufficiently mixed so that the mixture is substantially homogeneous. The temperature of the mixture is monitored to ensure the temperature of the mixture is still within a desired temperature range. If necessary, the mixture is heated to bring the temperature of the mixture with the desired range. The mixing process is repeated until all of the components have been mixed into the composition.

When used for treating the pain associated with menstrual cramps, the pain relief composition of the present invention is applied to the patient's abdomen about 3 to 4 times a day. An amount of the pain relief composition used is selected based on the desired application area so as to provide a relatively thin layer of the pain relief composition over the entire affected area.

The pain relief composition of the present invention is described with reference to the following examples. These examples are provided as an illustration of the invention and are not intended to limit the scope of the invention.

EXAMPLE 1

A pain relief composition was prepared using the components and concentrations set forth in Table 1. The components were subjectively evaluated for color, smell and weight. Each of these characteristics was found to be of a satisfactory level. The components were then filtered through a Grade 2 filter. Next, the components were each heated to a temperature of between 35 and 38° C. using a water bath.

TABLE 1

| Component | Concentration (weight percent) |
| --- | --- |
| Aloe Vera oil | 5 |
| Camphor oil | 3 |
| Eucalyptus oil | 1 |
| Lemon oil | 1 |
| Orange oil | 1 |
| Peppermint oil | 84 |
| Rosemary oil | 5 |

The peppermint oil was found to have the highest hydrophil content and, as such, was the first component used in formulating the mixture. The rosemary oil was mixed at the specified concentration with the peppermint oil to prepare a homogeneous mixture. The process was then repeated separately mixing, in order, aloe, camphor, lemon and orange oils at the specified concentrations. After the addition of each component, the mixture was sufficiently mixed to prepare a substantially homogeneous mixture.

The pain relief composition was applied to the abdomen of a female who was experiencing a significant amount of discomfort associated with PMS. Within a short period of time after the pain relief composition was applied to the person's abdomen she noted a significant reduction of the discomfort associated with PMS. The reduced level of pain continued for more than 4 hours.

EXAMPLE 2

A pain relief composition was prepared using the components and concentrations set forth in Table 2. The components were subjectively evaluated for color, smell and weight. Each of these characteristics was found to be of a satisfactory level. The components were then filtered through a Grade 2 filter. Next, the components were each heated to a temperature of between 35 and 38° C. using a water bath.

TABLE 2

| Component | Concentration (weight percent) |
|---|---|
| Aloe Vera oil | 15 |
| Camphor oil | 3 |
| Eucalyptus oil | 1 |
| Lemon oil | 1.5 |
| Orange oil | 1.5 |
| Peppermint oil | 73 |
| Rosemary oil | 5 |

The peppermint oil was found to have the highest hydrophil content and, as such, was the first component used in formulating the mixture. The rosemary oil was mixed at the specified concentration with the peppermint oil to prepare a homogeneous mixture. The process was then repeated separately mixing, in order, aloe, camphor, lemon and orange oils at the specified concentrations. After the addition of each component, the mixture was sufficiently mixed to prepare a substantially homogeneous mixture.

The pain relief composition was applied to the abdomen of a female who was experiencing a significant amount of discomfort associated with PMS. Within a short period of time after the pain relief composition was applied to the person's abdomen she noted a significant reduction of the discomfort associated with PMS. The reduced level of pain continued for more than 4 hours.

EXAMPLE 3

A pain relief composition was prepared using the components and concentrations set forth in Table 3. The components were subjectively evaluated for color, smell and weight. Each of these characteristics was found to be of a satisfactory level. The components were then filtered through a Grade 2 filter. Next, the components were each heated to a temperature of between 35 and 38° C. using a water bath.

TABLE 3

| Component | Concentration (weight percent) |
|---|---|
| Aloe Vera oil | 15 |
| Calendula oil | 4 |
| Eucalyptus oil | 1 |
| Lemon oil | 1.5 |
| Orange oil | 1.5 |
| Peppermint oil | 72 |
| Rosemary oil | 5 |

The peppermint oil was found to have the highest hydrophil content and, as such, was the first component used in formulating the mixture. The rosemary oil was mixed at the specified concentration with the peppermint oil to prepare a homogeneous mixture. The process was then repeated separately mixing, in order, aloe, lemon, orange and calendula oils at the specified concentrations. After the addition of each component, the mixture was sufficiently mixed to prepare a substantially homogeneous mixture.

The pain relief composition was applied to the abdomen of a female who was experiencing a significant amount of discomfort associated with PMS. Within a short period of time after the pain relief composition was applied to the person's abdomen she noted a significant reduction of the discomfort associated with PMS. The reduced level of pain continued for more than 4 hours.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

What is claimed is:

1. A pain relief composition for relieving pain in a human body, the pain relief composition consisting essentially of a mixture of aloe vera oil, eucalyptus essential oil, lemon essential oil, orange essential oil, peppermint essential oil, and rosemary essential oil; wherein the peppermint essential oil is between about 65 and 84 percent by weight.

2. The pain relief composition of claim 1, wherein the concentration of aloe vera oil is between about 10 and 18 percent by weight.

3. The pain relief composition of claim 1, wherein the concentration of eucalyptus essential oil is between about 0.5 and 5.0 percent by weight.

4. The pain relief composition of claim 1, wherein the concentration of lemon essential oil is between about 0.5 and 5.0 percent by weight.

5. The pain relief composition of claim 1, wherein the concentration of orange essential oil is between about 0.5 and 5.0 percent by weight.

6. The pain relief composition of claim 1, wherein the concentration of peppermint essential oil is between about 65 and 80 percent by weight.

7. The pain relief composition of claim 1, wherein the concentration of rosemary essential oil is between about 2 and 10 percent by weight.

8. The pain relief composition of claim 1, and further comprising calendula essential oil.

9. The pain relief composition of claim 8, wherein the concentration of calendula essential oil is up to about 25 percent by weight.

* * * * *